(12) United States Patent
Zieris et al.

(10) Patent No.: US 10,278,790 B2
(45) Date of Patent: May 7, 2019

(54) STORAGE SYSTEM FOR MEDICAL INSTRUMENTS

(71) Applicant: Aesculap AG, Tuttlingen (DE)

(72) Inventors: Gerold Zieris, Mülheim (DE); Dieter Weisshaupt, Immendingen (DE); Serkan Bellikli, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 15/322,254

(22) PCT Filed: Jun. 17, 2015

(86) PCT No.: PCT/EP2015/063576
§ 371 (c)(1),
(2) Date: Dec. 27, 2016

(87) PCT Pub. No.: WO2016/000962
PCT Pub. Date: Jan. 7, 2016

(65) Prior Publication Data
US 2017/0143449 A1 May 25, 2017

(30) Foreign Application Priority Data
Jul. 1, 2014 (DE) .................. 10 2014 109 197

(51) Int. Cl.
*B25H 3/00* (2006.01)
*A61C 3/04* (2006.01)
(Continued)

(52) U.S. Cl.
CPC ............... *A61C 3/04* (2013.01); *A61B 50/20* (2016.02); *A61B 50/30* (2016.02); *A61B 50/34* (2016.02);
(Continued)

(58) Field of Classification Search
CPC ........... A61C 3/04; A61C 19/02; A61B 50/20; A61B 50/30; A61B 50/34;
(Continued)

(56) References Cited

U.S. PATENT DOCUMENTS 4,919,264 A    4/1990   Shinall
5,533,700 A *   7/1996   Porter ............... B60N 3/101
                                                             224/926
(Continued)

FOREIGN PATENT DOCUMENTS

CN      201701325 U    1/2011
CN      103876777 A    6/2014
(Continued)

OTHER PUBLICATIONS

International Search Report and Written Opinion for International Application No. PCT/EP2015/063576, dated Feb. 9, 2015, 9 pages.
(Continued)

*Primary Examiner* — Jacob K Ackun
*Assistant Examiner* — Jenine Pagan
(74) *Attorney, Agent, or Firm* — RatnerPrestia (57) ABSTRACT

A receiving sleeve receives surgical instruments. A holding device for storing and cleaning surgical instruments includes at least one receiving sleeve. A surgical instrument set includes a holding device and/or receiving sleeve. The receiving sleeve and the holding device have a light construction which allows the maximum flow of fluid to instruments held in the receiving sleeve or holding device. The receiving sleeve includes a cylindrical hollow body with a plurality of peripherally spaced inner clamping arms which have punctiform or linear engagement sections that are adjusted to come into contact with an inserted tool in a force-fit or form-fit manner for holding the tool within the receiving sleeve at a radial distance to the cylindrical body.

16 Claims, 5 Drawing Sheets

(51) Int. Cl.
  *A61C 19/02* (2006.01)
  *A61B 50/34* (2016.01)
  *A61B 50/20* (2016.01)
  *A61B 50/30* (2016.01)
  *A61B 50/00* (2016.01)

(52) U.S. Cl.
  CPC ........ *A61C 19/02* (2013.01); *A61B 2050/006* (2016.02); *A61B 2050/0074* (2016.02)

(58) Field of Classification Search
  CPC ...... A61B 2050/0074; A61B 2050/006; B25B 23/2007; B25B 23/0035; B25B 23/0042
  USPC .............. 206/370, 372, 373, 368, 369, 349; 422/298; 81/184
  See application file for complete search history.

(56) References Cited

U.S. PATENT DOCUMENTS

| | | | | |
|---|---|---|---|---|
| 5,651,941 | A * | 7/1997 | Stark | B01L 9/06 220/676 |
| 5,897,090 | A * | 4/1999 | Smith | B01L 9/06 206/306 |
| 5,918,740 | A | 7/1999 | Berry, Jr. | |
| 5,941,366 | A * | 8/1999 | Quinlan | B65G 17/002 198/465.1 |
| 6,176,369 | B1 * | 1/2001 | Petrovic | B65G 17/002 198/803.14 |
| 6,274,092 | B1 * | 8/2001 | Itoh | B01L 9/06 206/443 |
| 6,343,690 | B1 * | 2/2002 | Britton | B65G 17/002 198/803.6 |
| 6,494,822 | B1 * | 12/2002 | Hopkins | B23Q 3/15553 211/69 |
| 6,971,506 | B2 * | 12/2005 | Hassinen | G01N 35/04 198/803.14 |
| 7,066,329 | B2 * | 6/2006 | Riley | A61C 3/04 206/369 |
| 7,485,264 | B2 * | 2/2009 | Itoh | B01L 9/06 206/443 |
| 9,114,394 | B2 * | 8/2015 | Yanez | B01L 9/06 |
| 2003/0215370 | A1 * | 11/2003 | Itoh | B01L 9/06 422/400 |
| 2005/0016886 | A1 | 1/2005 | Riley | |
| 2008/0230423 | A1 | 9/2008 | Loeffler | |
| 2012/0094249 | A1 | 4/2012 | Abene | |
| 2012/0138495 | A1 | 6/2012 | Bettenhausen | |
| 2013/0046289 | A1 | 2/2013 | Allen | |
| 2013/0064709 | A1 | 3/2013 | Allen | |
| 2014/0170592 | A1 | 6/2014 | Johansson | |
| 2014/0171801 | A1 | 6/2014 | Starr et al. | |
| 2014/0202903 | A1 * | 7/2014 | Dassonville | A61C 3/04 206/370 |

FOREIGN PATENT DOCUMENTS

| | | |
|---|---|---|
| DE | 19916025 | 12/2000 |
| DE | 202007016144 | 2/2008 |
| WO | 2005053597 | 6/2005 |

OTHER PUBLICATIONS

German Search Report for German Application No. 10 2014 109 197.3 with translation, dated Mar. 10, 2015, 9 pages.
English translation of Chinese Office Action for Chinese Application No. 201580036147.9, dated Oct. 8, 2018—10 pages.

* cited by examiner

STORAGE SYSTEM FOR MEDICAL INSTRUMENTS

RELATED APPLICATION(S)

This application is the United States national phase entry under 35 U.S.C. § 371 of International Application No. PCT/EP2015/063576, filed Jun. 17, 2015, which is related to and claims the benefit of priority of German Application No. DE 10 2014 109 197.3, filed Jul. 1, 2014. The contents of International Application No. PCT/EP2015/063576 and German Application No. DE 10 2014 109 197.3 are incorporated by reference herein in their entireties.

FIELD

The present invention relates to a storing system for medical instruments, and more particularly to a storing system for dental instruments.

BACKGROUND

In modern surgery, a plurality of different instrument heads/tools such as e.g. drilling or milling heads are used, which each can be detachably attached on/put into a hand piece comprising an instrument drive. This allows the surgeon to change the instrument head (attached on/put into a hand piece) depending on the requirement of the application during use of the hand piece. In order to give the surgeon the most easy access to these instrument heads (which are referred to as tools in the following), said tools are usually stored in a sorted manner in a surgical tool set. In order to avoid damages on the tools and ensure a quick finding of a required tool, the tools are not stored in loose manner, but are held in receiving sleeves which are inserted in a hole array of the tool set or fixed therein. In order to make it easier for the surgeon to find the respectively required tool, the receiving sleeves have a color coding in many cases. In addition, it is possible to place a template comprising printed OP paths on the receiving sleeves, to further simplify the selection of the respectively required tool.

Conventional tool sets for the storing/keeping of surgical tools can be purchased from various suppliers and hence belong to the general prior art. These known tool sets essentially consist of a plastic or metal box comprising a hinged cover which can be opened and closed, in which an intermediate shelf or an insert being placed between the bottom and the cover of the box so as to be parallel to the bottom of the box. The intermediate shelf has round holes into which (plastic) receiving sleeves for receiving tools are inserted. Here, the receiving sleeves are designed as one-piece, massive hollow cylinders which each have a receiving opening for a particular surgical tool. Surgical tools, in particular dental tools or rotary tools of this kind, have a distal tool engagement section and a proximal shaft portion, wherein receiving sleeves having different diameters of the tool receiving openings allow the correct and exact mounting of tools having different shaft diameters. Further, the receiving sleeves are provided with a color coding so that it is easier for a surgeon to find a required tool, wherein a printed template is preferably provided which can be laid over the receiving sleeves and is imprinted with OP paths and designations of the tools respectively received in one of the receiving sleeves.

Apart from the careful storing of surgical tools and their fast retrievability during a surgical operation, the thorough and frequent cleaning and, where required, the sterilization of surgical tools is of utmost importance.

Whereas conventional tool sets are well suited for storing surgical tools and also ensure a quick retrieval of the respectively required tool during a surgery, a disadvantage of said conventional tool sets relies in that surgical tools have to be taken out of a conventional tool set (storage box) for cleaning purposes and thereafter have to be shelved again therein, because the cleaning of tools is impossible or only hardly possible with conventional instrument sets when the tools are inserted in the instrument set (storage box). This is mainly due to the massive construction of the receiving sleeves and of the instrument set itself, largely preventing the received tools from being washed with cleaning fluids or gases. The plastic box of the tool set is difficult to access for cleaning fluids and the massive construction of the receiving sleeves and their large contact surface with the received instruments cause an only insufficient cleaning of the portions of the tools received in the receiving sleeves.

As there are up to 90 different surgical tools which may be received in a single tool set, the removal of all tools for cleaning them and a subsequent re-equipment of the tool set is very time-consuming. Moreover, surgical tools have to be gently treated for a long service life, in order to prevent any dulling or damaging of tips or edges, for instance, and the tools have to be thoroughly cleaned after each application, further enlarging the expenditure of time.

It also happens that soilings accumulate even on the tool set itself if it is repeatedly used for receiving contaminated tools for instance during a surgery. In the event that a contaminated tool is put back into a receiving sleeve, any contaminations such as bone splinters or blood clinging on the tool may remain adhered in the hollow cylinder of the receiving sleeve or fall onto the template laid on the receiving sleeves. It is also required that the space between the bottom of the tool set and the intermediate shelf in which the receiving sleeves are inserted is kept very clean. This is why conventional tool sets have to be dismantled for cleaning the receiving sleeves and the remaining constituent parts of the set (plastic box, cover, intermediate shelf); subsequently, the various constituent parts of the tool set have to be cleaned individually and then the set must be assembled again afterwards. The expenditure of time is very large here, too, and the numerous steps of the cleaning method (dismantling into individual parts, cleaning each individual part) offers many occasions for damaging the tool set or for operator errors during cleaning. As the massive construction of the receiving sleeves hinders the cleaning liquids from penetrating into the receiving opening of the receiving sleeves, a manual subsequent cleaning process has to be carried out, if need be.

In order to withstand high temperatures during sterilization, any plastic portions of conventional tool sets have to be made from a special temperature-resistant plastic, increasing the production costs. In addition, soilings adhere on a plastic material due to its positive superficial charge for a longer time than on other materials such as metals, for instance, which makes the cleaning of the tool set still more difficult. Even in drying the tool set after the cleaning process, the massive construction of conventional tool sets and their applicable material plastics prove to be disadvantageous.

Thus, the prior art knows tool sets and receiving sleeves for surgical instruments which due to the massive construction of the receiving sleeves and the tool sets do not allow a cleaning of the received surgical instruments in the equipped state of the tool set (storage box).

SUMMARY

Starting from the prior art described above, the invention is based on the object to provide a receiving sleeve, a holding device for said receiving sleeve and a surgical instrument set which allow an efficient and simplified cleaning of the tool set (preferably in the equipped state) as well as of the surgical instruments contained therein.

This object is achieved by a receiving sleeve and a surgical tool set as described herein.

In essence, the basic idea of the invention is to design both the receiving sleeve and the entire tool set (i.e. the reception box comprising a sleeve holding device and a receiving sleeve) so as to be as permeable as possible for cleaning or drying fluids by means of a filigree construction, so that the greatest possible quantity of the cleaning or drying fluid can find its way to the tools received in the tool set. Due to a thereby simplified cleaning of surgical tools and entire tool sets, the expenditure in time needed for their preparation and the costs for providing them are lowered. The manufacturing and acquisition costs of receiving sleeves for surgical tools and of tool sets can be reduced as well.

A further basic idea of the invention essentially is to provide the receiving sleeves inserted in the tool set with a sort of inner tool support which holds the inserted tool substantially in a punctiform or linear manner, so that (radial) clearances remain between the inserted tool and the receiving sleeve, which can be used for extensive flows of the cleaning fluid around the inserted tool.

The gist of the present invention accordingly is to realize the receiving sleeve as well as the constituent parts of the holding device which supports the receiving sleeve and of the tool set (box) which receives the holding device, into which the receiving sleeve is inserted, as well as any further additional parts of the tool set according to the invention (in a filigree/framework construction) as perforated bodies with a light design, in order to ensure a circumferential permeability for cleaning fluids and create only small contact surfaces to the tool. This light construction is in contrast to the massive construction of the receiving sleeves, holding devices for receiving sleeves and tool sets (including box, holding device and receiving sleeves) known from prior art and allows to leave the tool in the receiving sleeve and in the tool set (tool box) if the latter is supposed to undergo a cleaning/sterilization procedure. With this, the tool remains protected against external influences in the course of a cleaning procedure. At the same time, not only the tool is cleaned/sterilized, but also the receiving sleeve and the entire tool set.

In the sense of this application, a light construction is to be understood as a construction of a body/box in which the body/box comprises as many openings as possible and is perforated to the largest extent. A massive construction, however, is to be understood in the sense of this application as a construction of a body/box in which the body/box has few to no openings and hence is perforated to a low degree or is not perforated at all. Stated in other words, the term "light construction" is preferably defined in that the total area of the openings/recesses in the receiving sleeve/in the box is larger than the total area covered by the material of sleeve and box.

According to the invention, the receiving sleeve consists of a body having a light design (framework construction) according to above definition in the form of a hollow cylinder/hollow body comprising an axial tool receiving/insertion opening provided at a first axial end and into which surgical tools can be inserted, wherein the hollow cylinder/hollow body of the receiving sleeve being designed to minimize the contact surface between the receiving sleeve and a tool received therein and allow the maximum fluid flow (radially) through the hollow body of the receiving sleeve and toward the tool received in the receiving sleeve. Preferably, the receiving sleeve is made in one piece from plastics, for instance in an injection-molding method or according to a rapid prototyping method (sintering method) and is distinguished by a preferably planar surface without any gaps or undercuts so as to counteract an accumulation of soilings.

In one embodiment, the receiving sleeve has its inner side provided with a number of elastically deformable protrusions (or clamping arms/holding claws) which preferably form a funnel within the hollow cylinder of the receiving sleeve, said funnel narrowing in the insertion direction of a tool to be received. By/upon inserting the surgical tool, the diameter of the cavity radially delimited by the clamping arms is radially expanded and the clamping arms are pushed outward in the radial direction in a resilient manner. The arising elastic tension of the clamping arms clamps the inserted tool in the cavity of the hollow cylinder between the clamping arms. Here, the clamping arms are formed preferably in such a manner that the contact surface between the clamping arms and the received tool is as small as possible (linear and/or punctiform). As the surface of the tool forms a site of contact with the hollow body of the receiving sleeve only at the points/lines defined by the clamping arms, the major part of the surface of said portion of the tool which is received in the receiving sleeve is not in contact with the hollow body of the receiving sleeve and hence the cleaning fluid may wash around it.

It is particularly advantageous that it is very easy to implement different receiving sleeves for receiving surgical tools having various shaft diameters by varying the diameter of the hollow cylinder and adapting the elastic deformability of the protrusions/clamping arms.

In an alternative embodiment, the clamping arms on the inner side of the receiving sleeve are not formed in one piece with the hollow body of the receiving sleeve, but are manufactured separately e.g. from metal and embedded in the hollow body of the receiving sleeve. Such a manufacture of the clamping arms has an advantageous effect on the service life and the ruggedness of the receiving sleeve.

In a further embodiment, the receiving sleeve has its inner side provided with a number of rigid, axially extending protrusions (or axially extending guiding arms/longitudinal ribs) which preferably form a funnel within the hollow cylinder/hollow body of the receiving sleeve, said funnel narrowing in the insertion direction of a tool to be received. Preferably, the protrusions/guiding arms additionally constitute a catching bottom (stop) in the hollow cylinder at the other end portion (opposite the insertion opening) of the receiving sleeve in order to prevent a tool from being inserted too deep into the receiving sleeve. The rigid guiding arms prevent a tool with an excessively large shaft diameter from being inserted into the receiving sleeve, as the guiding arms (other than the clamping arms) cannot be elastically deformed or only to a negligible extent and in this way clearly define a maximum shaft of an insertable tool. A receiving sleeve according to the invention may comprise only the guiding arms in a specific number, only the clamping arms in a specific number or even a combination of guiding and clamping arms.

In order to allow the receiving sleeve to be inserted and firmly anchored in a holding device preferably consisting of two parallel and spaced perforated plates or arrays, the receiving sleeve in one embodiment of the invention has its outer side (shell surface) provided with at least one elastically deformable, radially protruding protrusion or retaining wedge. If the receiving sleeve is inserted for instance in a hole of the holding device (hole array/perforated plate), the protrusion/retaining wedge is pressed inwards in the radial direction of the hollow cylinder due to the limitation of the hole. Due to the elastic tension of the retaining arm, the receiving sleeve is held in position in the hole of the hole array by the protrusion engaging behind the hole of the holding device (perforated plate) and hence is axially supported on the holding device (hole array/perforated plate) when the receiving sleeve is axially inserted into the holding device (perforated plate) to the full extent.

In a preferred embodiment of the receiving sleeve according to the invention, said sleeve additionally comprises a surrounding annular protrusion (collar) along the circumference of the hollow cylinder in the area of the insertion opening and at an axial distance to the retaining wedge, said collar resting on a hole array which has preferably round holes and hence preventing the receiving sleeve from performing an undesired movement in the insertion direction and from falling through/being pushed through a round hole of the array when the receiving sleeve is in the state of being inserted in the holding device. With this, the holding device/hole array is axially fixed between the collar and the retaining wedge. Preferably, the surrounding protrusion comprises a flat area on its side facing the insertion opening of the receiving sleeve, so that a printed template can be placed on the flattened side of the annular protrusion in a form-fit manner. Further preferred, the surrounding annular protrusion comprises recesses/axial protrusions on its side facing away from the insertion opening of the receiving sleeve, whereby the axial contact surface between the collar and the array of the holding device is reduced and possible soilings accumulating between the receiving sleeve and the holding device can be efficiently washed away by the cleaning fluid.

In a further embodiment of the present invention, the receiving sleeve has its other axial end (opposite the insertion opening) provided with a number of axially extending, rigid protrusions (positioning studs) which hold the receiving sleeve in position if the latter is fully inserted in the holding device. Concerning this, the following should be mentioned:

A holding device according to the invention comprises for instance a first hole array (perforated plate) having round holes into which a respective receiving sleeve is inserted and further comprises another, second array (perforated plate) e.g. provided with cornered recesses/holes and arranged to be parallel to said hole array; the recess areas of said second array are smaller than the surface areas of the round holes of the first array, and said cornered recesses are in alignment with the round holes of the first hole array.

In this exemplary embodiment, the rigid positioning studs of the receiving sleeve are formed with a cornered cross-section, so that they engage the corners of the cornered recesses of the second array in a form-fit manner and are able to prevent any displacement or rotation of the receiving sleeve. If a second array is used which has recesses/holes of another shape, it is within the scope of the invention to correspondingly adapt the positioning studs of the receiving sleeves, so that the positioning studs engage a respective recess/hole of the second array in a form-fit manner.

In one embodiment, the receiving sleeve further comprises at its lower end at least one elastically deformable, hook-shaped and axially extending protrusion (latching arm) which is formed similar to the positioning studs such that it is capable of engaging for instance one corner of a cornered recess of the second array of a holding device in a form-fit manner and/or axially engaging behind the preferably cornered recess. By way of example, if a receiving sleeve is inserted in a holding device according to the invention having two arrays arranged in parallel fashion, from which the first array comprises round holes and the second array comprises cornered recesses/holes which are in alignment with the round holes of the first array, the receiving sleeve is pushed through a round hole of the first array until the collar of the hollow cylinder comes to rest on the first array and axially fixes the first array between itself and the retaining wedge. Here, the at least one elastically deformable latching arm at the other end of the hollow body is pushed through the recess/the cornered hole of the second array until the hook-shaped protrusion of the latching arm snaps in place behind the second array and in this way prevents the receiving sleeve from moving and falling out contrary to the direction of insertion. As the recessed area of the second array is smaller than the hole area of the first array, the receiving sleeve adapted to the hole area of the first array is axially supported on the second array by its hollow body and in this way fixes the second array between the hollow body and the axially projecting latching arm. Thus, the axial distance between the two arrays is determined as well.

In other words, if a receiving sleeve comprises in one embodiment both at least one latching arm and a retaining arm (retaining wedge), the receiving sleeve defines the distance between the first and the second array, as the first array comes to lie on the hook-shaped protrusion of the retaining arm and the second array is held in position by the hook-shaped protrusion of the latching arm.

A further aspect of the present invention relates to a tool set for storing and cleaning surgical tools/dental tools and comprises at least one receiving sleeve of the invention according to the above description. Furthermore, the tool set comprises several outer walls and at least one inner wall (bottom and/or an insert) as the holding device, which has the shape of two parallel and spaced hole arrays according to the above description, into which the at least one receiving sleeve according to the invention is inserted or can be inserted.

In its basic design, the tool set has the construction of a box/cage comprising a bottom (perforated plate or wire mesh), a cover (perforated plate or wire mesh) preferably with a handle, and several outer walls (frame). It is preferred that the cover has at least two of its outer walls provided with a centering plate which facilitates an exact placement of the cover onto the box. As an alternative or in addition, the cover may comprise a centering pin on at least one of its corners, which engages a centering hole in at least one corresponding corner of the bottom/side wall/box and hence ensures an exact placement of the cover onto the box. In the closed state, the cover is held on the box preferably by a closure. Here, the closure may have the shape of a resilient bracket which can be pushed onto the closed holding device from outside and encompasses the cover and the box/bottom of the closed holding device. Alternatively, it is possible to use a springy metal sheet or an articulated metal sheet which encompasses the box/bottom of the closed holding device and additionally engages in a recess in a side wall of the cover.

It is preferred that the bottom of the box/cage forms a holding device according to the previous description for the receiving sleeves according to the invention. As an alternative or in addition, the tool set may comprise an inner wall/insert/intermediate shelf preferably in the shape of two parallel and spaced metal sheets which are arranged parallel to the bottom of the box and each comprise a stamped hole array according to the previously described holding device. The receiving sleeves according to the invention can be inserted into the holes of these hole arrays in the manner described above.

In one embodiment of the tool set according to the invention, the outer walls/side walls and the at least one inner wall/the holding device have a light construction and are manufactured, for instance, from a perforated material, preferably from a metal grid or screen or a perforated plate. This has the advantage that cleaning fluids can easily enter the box and the holding device and wash around the tools received in the receiving sleeves. To this end, the holding device according to the invention as well as the receiving box do not have to be dismantled for cleaning and it is also not necessary to remove the received tools for this purpose, but the entire holding device and the box can be cleaned in the equipped state without impairing the thoroughness of the cleaning of the holding device/the box or of the tools contained therein. As it is not required any longer to individually take out small parts such as surgical tools from the receiving sleeves for cleaning purposes and to clean them separately and the holding device as well as the box do not have to be dismantled and assembled again after the cleaning process, the expenditure of time required for the cleaning of tools, holding device and box is significantly reduced. In addition, the cleaning method is less prone to operator errors and is more gentle to the surgical tools which remain in the receiving sleeves throughout the entire procedure, whereby damages on the tools are avoided and their service life in prolonged. As fewer hand movements are required for cleaning the tools, the holding device according to the invention as well as the box, the achievement of sterility of the tools is additionally facilitated.

The use of metal in the manufacture of the holding device and/or of the box also has the advantage that the metal can withstand the high temperatures for instance during the sterilization, only few soilings remain adhered on the metal surface and the drying procedure of the holding device/of the box is carried out in a shorter time and more thoroughly than with a holding device/box which is manufactured from plastics.

Apart from the receiving sleeves for surgical tools, the holding device according to the invention may also comprise other storage elements for surgical instruments, for instance storage elements of the Aesculap instrument organization system (AIOS) which is known from prior art. The design of the holding device can be correspondingly adapted depending on the number of tools which have to be stored in receiving sleeves or other storage elements. In one exemplary embodiment, an amount of 80% of the surface area of the holding device represents a hole array for inserting receiving sleeves, whereas the residual amount of 20% of the surface area represents a raster of a different design for attaching other instruments having a construction which is known, for instance, from AIOS storage elements. If it is required to store so many tools and other instruments that the total area of the one holding device in the form of the correspondingly formed bottom of the tool set is not sufficient, it is possible, for instance, to equip the bottom which first was intended to be the holding device with a raster for attaching e.g. AIOS storage elements of known design, and an intermediate shelf may be additionally installed parallel to the bottom, which will then form the holding device of the previously described construction, into which receiving sleeves are inserted. This intermediate shelf consists of the previously described first and second arrays, which comprise for instance round holes and preferably cornered recesses/holes, respectively, into which receiving sleeves according to the described construction are inserted, wherein the receiving sleeves are held in position by possible retaining arms, positioning studs and latching arms and, if need be, determine the distance of the arrays of the intermediate shelf as described above.

Such an intermediate shelf preferably comprises at least one corner foot which engages in at least one corresponding recess in an inner protrusion on an outer wall of the box and in this way ensures an exact placement of the intermediate shelf on the bottom part of the box.

In one embodiment, the tool set alternatively comprises a plastic box which contains a holding device according to the invention in the form of an intermediate shelf. In this case, the surgical tools can be stored in the tool set according to the invention, the tools remain in the holding device for cleaning them and the holding device can be taken out of the tool set/box in the equipped state and then be cleaned. After the cleaning process, the equipped holding device is inserted in the plastic box again. The plastic box of the tool set has a massive construction, which has the advantage that the sterility of the surgical tools can be guaranteed over a prolonged period of time; nevertheless, the cleaning of surgical tools is considerably simplified.

BRIEF DESCRIPTION OF THE DRAWING FIGURES

Further features and advantages of the present invention will be apparent from the following exemplary description of a particularly preferred embodiment of the invention on the basis of the Figures in which.

DETAILED DESCRIPTION

Figure 4:
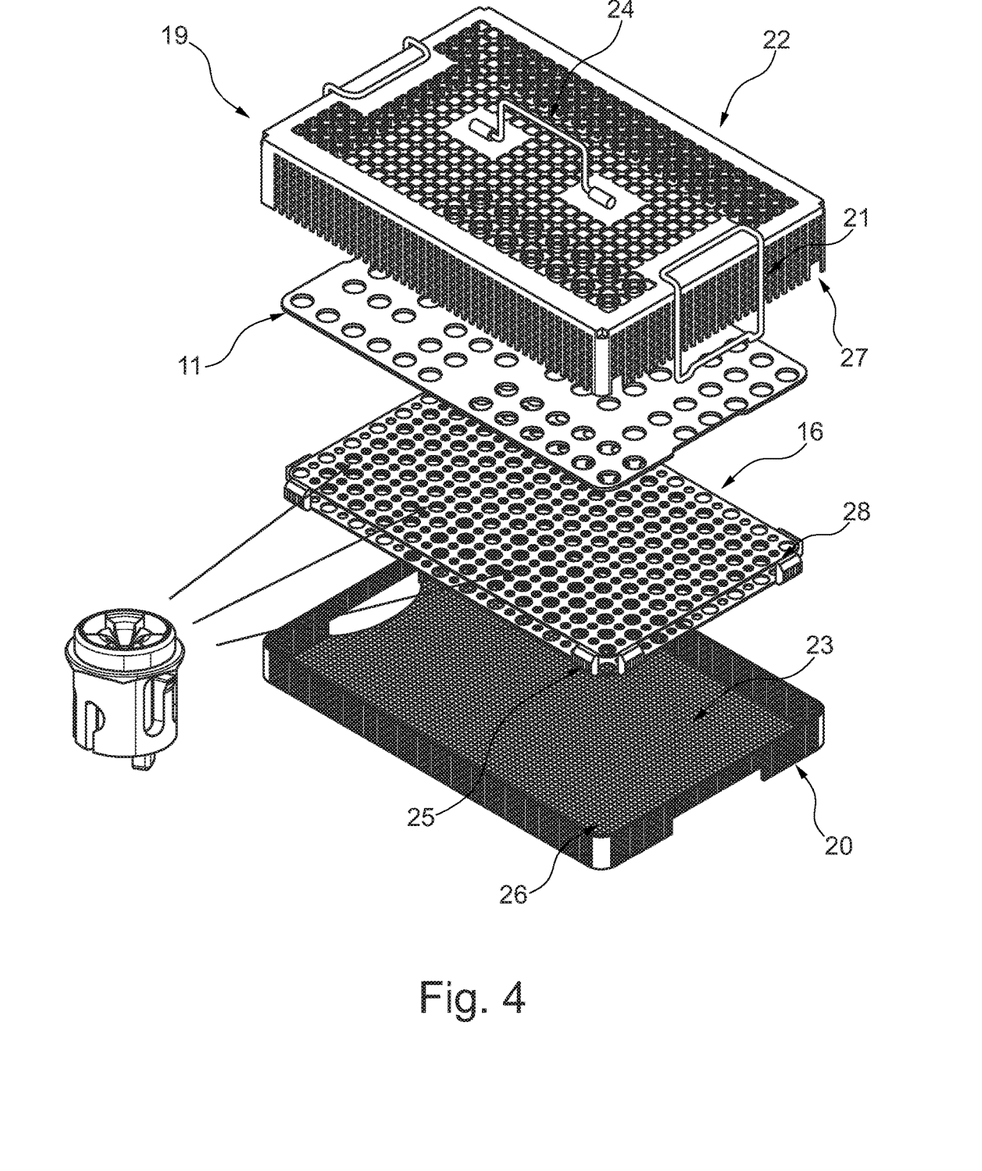
FIG. 4 shows a holding device comprising an intermediate shelf for receiving sleeves and a bottom part for housing further instruments such as so-called AIOS storage elements.
Figure 5A:
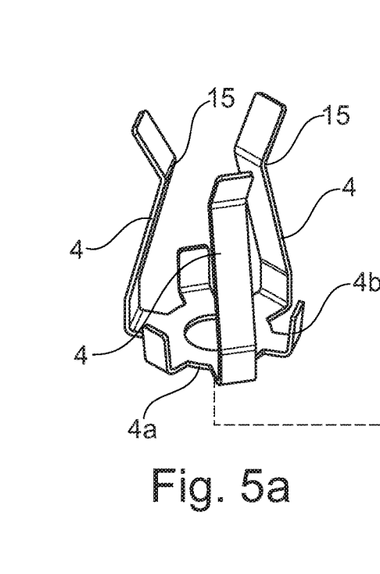
FIGS. 5a, 5b and 5c show components of a receiving sleeve of the present invention according to an alternative embodiment.
Figure 5B:
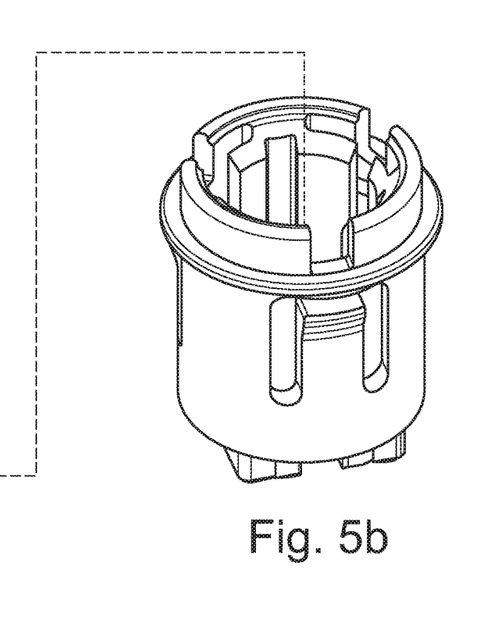
Figure 5C:
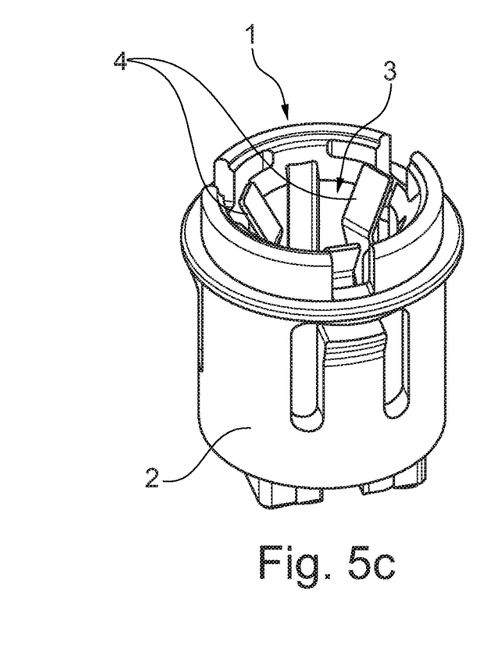

With reference to FIG. 4, a tool set 19 according to the invention comprising an intermediate shelf 16 for tool-receiving sleeves 1 according to the invention and a bottom part 20 for attaching AIOS storage elements will be described first.

In its basic design, the tool set 19 according to FIG. 4 has the construction of a box having a bottom part 20 preferably designed as a holding device for receiving sleeves 1, a cover 22 including a handle 24 and several outer walls (frame). In addition, the tool set 19 comprises a closure 21 in the form of a springy bracket which can be attached on the closed box from outside and encompasses the cover 22 and the bottom part 20 of the closed box.

Furthermore, the tool set 19 preferably comprises an intermediate shelf 16 as a (further) holding device which allows for the insertion of receiving sleeves 1 according to the invention as will be described in the following. A printed template 11 can be placed on the intermediate shelf 26. As an alternative or in addition, the bottom part 20 of the tool set 19 comprises a raster 23 for attaching AIOS storage elements.

The outer walls, the cover 22, the bottom part 20 and the optional intermediate shelf 16 of the tool set 19 have a light construction, i.e. are made from a perforated material, here from a metal grid or perforated plates. This has the advantage that the cleaning fluids can easily enter the tool set 19 and flow around the tools 14 received in the receiving sleeves 1. To this end, the tool set 19 according to the invention does not have to be dismantled for cleaning and it is also not necessary to remove the received tools 14 for this purpose, but the entire tool set 19 can be cleaned in the equipped state without impairing the thoroughness of the cleaning of the tool set 19 or of the tools 14 contained therein.

The intermediate shelf 16 preferably comprises at least one corner foot 25 which engages at least one corresponding recess 26 in a protrusion on an outer wall of the bottom part 20 of the tool set 19 and in this way ensures an exact placement of the intermediate shelf 16 on the bottom part 20 of the tool set 19 and holds the intermediate shelf 16 in position. The cover 22 further comprises a centering pin 27 on at least one of its corners, said centering pin engaging a hole 28 in at least one corresponding corner of the intermediate shelf 16 and thus ensures an exact placement of the cover 22 on the box.

Figure 3:
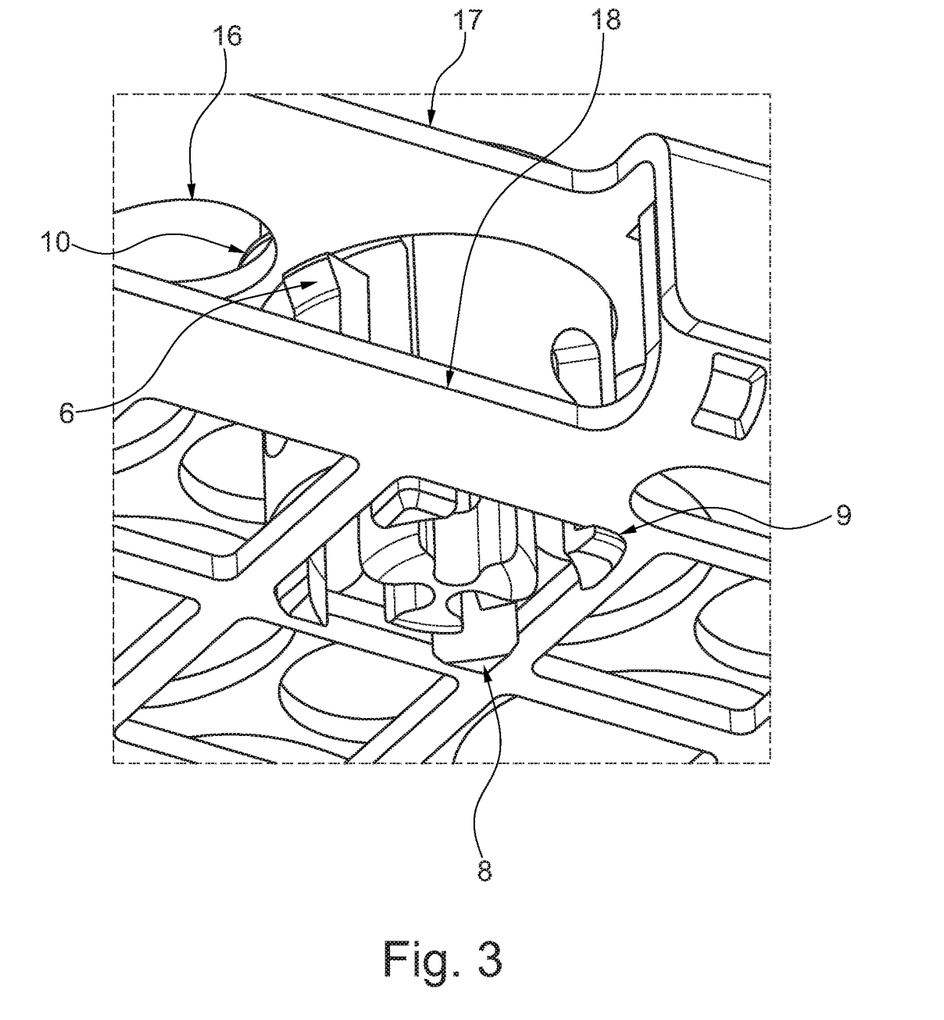
FIG. 3 shows a receiving sleeve which is inserted in an intermediate shelf of a holding device according to the invention.

The holding device for the receiving sleeves 1 in the form of the bottom part 20 and/or the intermediate shelf 16 is formed according to FIG. 3 from two parallel and spaced, perforated plates 17, 18 which are preferably connected to each other. The one perforated plate 17 is provided with round holes, and the other perforated plate 18 is provided with preferably rectangular recesses/holes, wherein said holes of the two perforated plates 17, 18 being (coaxially) arranged to overlap such that a receiving sleeve 1 can be inserted in two superimposed holes of the two perforated plates 17, 18.

Figure 1A:
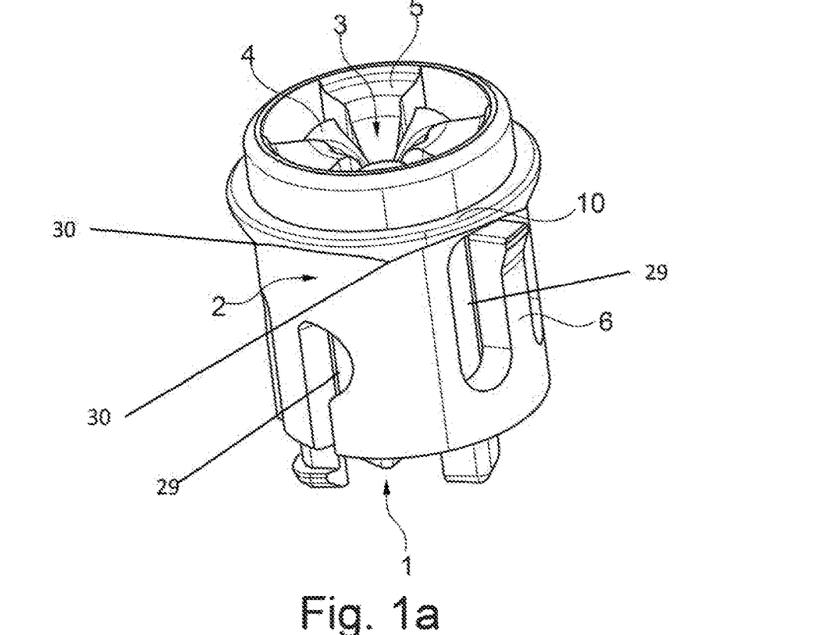
FIG. 1a shows a receiving sleeve according to the invention for a surgical tool, wherein the receiving sleeve is shown as seen from the receiving sleeve's first axial end.

FIG. 1*a* shows, in a perspective view as seen in the insertion direction of a tool 14, a receiving sleeve 1 according to the invention comprising a hollow body (or hollow cylinder) 2 having a light construction (filigree design) comprising an axial tool receiving opening 3 at its first axial end into which surgical tools 14 can be inserted. The hollow body having a light construction has radial openings 29. Here, the receiving sleeve 1 is made in one piece from plastics preferably in an injection-molding method or rapid prototyping method (sintering method). On its inner side, the receiving sleeve 1 comprises three or more elastically deformable, axially extending clamping arms 4 which preferably form a funnel within the hollow cylinder 2 of the receiving sleeve 1, said funnel narrowing in the insertion direction of a tool 14 to be received. By inserting a surgical tool, preferably a rotary tool (having a tool shaft) 14, the diameter of the cavity radially delimited by the clamping arms 4 is expanded and the clamping arms 4 are pushed radially towards outside. The elastic tension of the clamping arms 4 clamps the inserted tool 14 in the cavity of the hollow cylinder 2 between the clamping arms 4. In this arrangement, the clamping arms 4 are preferably designed such that the contact surface 15 between the clamping arms 4 and the received tool 14 is as small as possible (punctiform/linear). Moreover, the clamping arms hold the tool so as to be radially spaced from the hollow body 2.

By varying the diameter of the hollow cylinder/hollow body 2 and adapting the elastic deformability of the clamping arms 4, different receiving sleeves 1 for receiving surgical tools 14 having various shaft diameters can be formed easily. Alternatively, it would also be possible to design the clamping arms 4 on the inner side of the receiving sleeve 1 such that they are not formed in one piece with the hollow body 2 of the receiving sleeve 1, but are individually made e.g. from metal and embedded in the hollow body 2 of the receiving sleeve 1. Such a manufacture of the clamping arms 4 has an advantageous effect on the service life and the ruggedness of the receiving sleeve 1.

Furthermore, the receiving sleeve 1 has its inner side provided with three or more rigid guiding arms/longitudinal ribs 5 which are arranged within the hollow cylinder 2 of the receiving sleeve 1 between the clamping arms 4 as seen in the circumferential direction and likewise form a funnel narrowing in the insertion direction of a tool 14 to be received. The rigid guiding arms/longitudinal ribs 5 prevent a tool 14 having an excessively large shaft diameter from being inserted into the receiving sleeve 1, as the guiding arms 5 (in contrast to the clamping arms 4) cannot be elastically deformed and thus clearly define a maximum shaft diameter of an insertable tool 14.

In order to allow the receiving sleeve 1 to be inserted in the holding device consisting of the two arrays 17, 18 and to be firmly anchored therein, as is shown in particular in FIG. 3, the receiving sleeve 1 has its outer side/shell surface according to FIG. 1*a* additionally provided with at least one elastically deformable retaining arm/retaining wedge 6. By way of example, if the receiving sleeve 1 is inserted into a round hole of the one hole array 17 (see FIG. 3) of the previously described holding device, the retaining arm/retaining wedge 6 is pressed inwards in the radial direction of the hollow cylinder 2 due to the radial limitation of the hole. Due to the developing elastic tension of the retaining arm/retaining wedge 6, the retaining arm/retaining wedge 6 engages behind the hole array 17 as soon as the receiving sleeve 1 arrives at the axial position in the round hole of the one hole array 17. To this end, it is advantageously provided that the free end of the retaining arm/retaining wedge 6 facing the receiving opening 3 is designed as a protrusion/claw which protrudes radially outward and axially rests behind the one hole array 17 in a planar fashion.

Figure 1B:
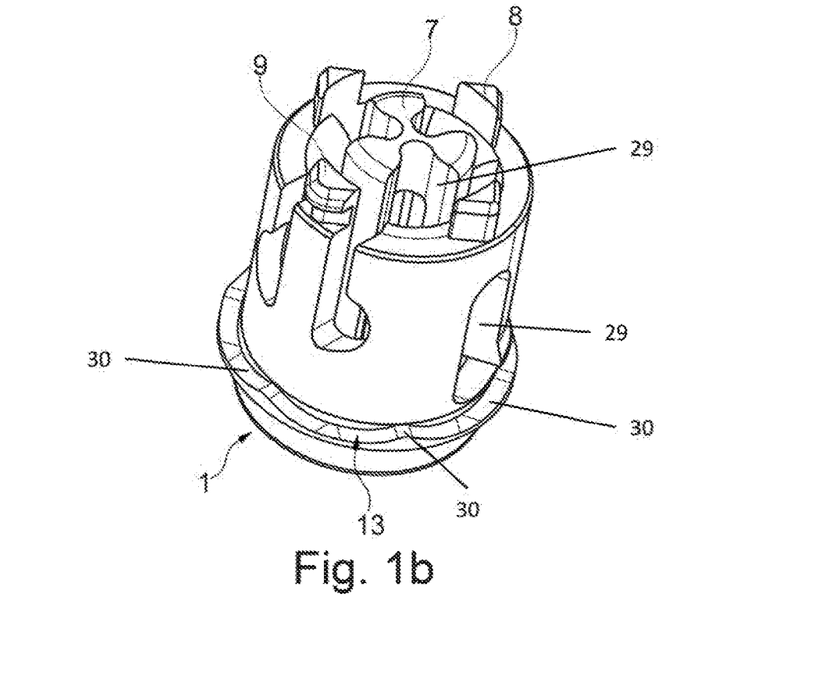
FIG. 1b shows the receiving sleeve of FIG. 1a as seen from the receiving sleeve's second axial end.

FIG. 1*b* shows the receiving sleeve 1 of FIG. 1*a* as seen in a perspective view contrary to the insertion direction of a tool 14.

It can be taken from this view how the guiding arms/longitudinal ribs 5 form a catching bottom/end stop 7 in the hollow cylinder 2 of the receiving sleeve 1 in order to prevent a tool 14 from being inserted too deep into the receiving sleeve 1. Specifically, the guiding arms 5 are interconnected by a transverse web at their axial ends opposite the tool insertion end, said transverse web representing the catching bottom/end stop 7.

The receiving sleeve 1 further comprises preferably three rigid positioning longitudinal studs 8 at its axial second end opposite the insertion end, which hold the receiving sleeve 1 in position if the latter is inserted in a holding device according to the above description. The positioning studs 8 of the receiving sleeve 1 have a cornered or triangular cross-section, so that they engage the corners of the cornered recesses of the other array 18 according to FIG. 3 in a form-fit manner and are able to prevent a displacement/rotation of the receiving sleeve 1 in the holding device. In case an array is used which has recesses/holes of any other shape, it is within the scope of the invention to correspondingly adapt the positioning studs 8 in terms of their geometry, so that the positioning studs 8 are able to engage a respective recess/hole of the other array 18 in a form-fit manner.

The receiving sleeve 1 also comprises at least one elastically deformable hook-shaped latching arm 9 on its axial end opposite the insertion opening 3, said latching arm 9 extending in axial direction similar to the positioning studs 8 and being formed such that it is able to engage, for instance, a corner of a cornered recess of the other array 18 of the holding device and to reach axially behind said array 18, as is shown in FIG. 3. By way of example, if a receiving sleeve 1 is inserted in a holding device according to the invention (bottom 20 or intermediate shelf 28) having two arrays 17, 18 arranged in parallel fashion, from which the first array 17 comprises round holes and the second array 18 arranged parallel thereto comprises cornered recesses which are in alignment with the round holes of the first array 17, the receiving sleeve 1 is pushed through a round hole of the first array 17 until the hollow cylinder 2 comes to rest on the second array 18, as is shown in particular in FIG. 3. Here, the at least one elastically deformable latching arm 9 is pushed through the recess of the second array 18 having the cornered holes until the hook-shaped protrusion of the latching arm 9 snaps in place behind the second array 18 and in this way prevents the receiving sleeve 1 from moving and falling out contrary to the direction of insertion.

Due to the action of the latching arm 9 and the retaining arm/retaining wedge 6 of the receiving sleeve 1, the receiving sleeve 1 preferably fixes the parallel distance between the first and the second array 17, 18, as the first array 17 comes to rest on the hook-shaped protrusion of the retaining arm 6 and the second array 18 is held in position by the hook-shaped protrusion of the latching arm 9.

The receiving sleeve 1 further comprises a surrounding annular protrusion or collar 10 along the circumference of the hollow cylinder 2 at its one axial end portion in the area of the insertion opening 3; when the receiving sleeve 1 is in the state of being inserted in the holding device, said collar rests on the first array 17 and axially clamps the first array 17 between itself and the radial protrusion of the retaining arm/retaining wedge 6, thus fixing the parallel distance between the first and the second array 17, 18 according to FIG. 3. This also prevents the receiving sleeve 1 from performing an undesired movement in the insertion direction and from falling through a hole of the first array 17. The surrounding protrusion 10 comprises a flat area on its side facing the first end of the receiving sleeve 1, so that a printed template 11 can be placed on the flattened side of the annular protrusion 10 in a form-fit manner. Furthermore, the surrounding annular protrusion 10 comprises recesses 13 and axial protrusions 30 on its side facing the second end of the receiving sleeve 1, whereby the contact surface 15 between the surrounding protrusion 10 and the first array 17 of the holding device is reduced and possible soilings accumulating between the receiving sleeve 1 and the holding device can be efficiently washed away by the cleaning fluid.

Figure 2:
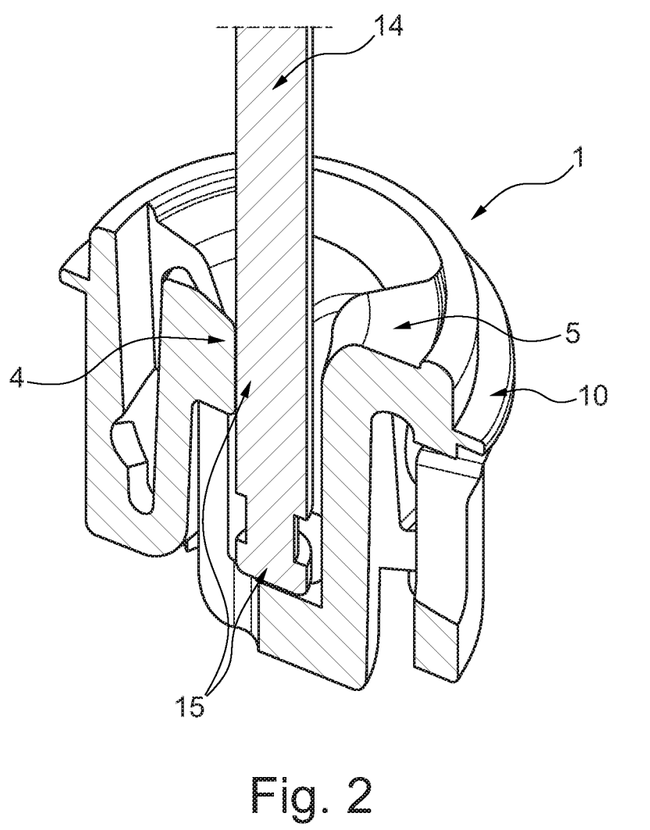
FIG. 2 shows a longitudinal section through a receiving sleeve including a surgical tool received therein.

FIG. 2 shows a cross-section through a receiving sleeve 1 including a surgical tool 14 received therein.

Accordingly, the tool 14 is in clamping contact with the clamping arms 4 and the catching bottom 7 of the receiving sleeve 1 only in the area of the defined contact points/lines 15. The clamping arms 4 are preferably formed here such that the contact points 15 between the clamping arms 4 and the received tool 14 are as small as possible. As the surface of the tool 14 rests against the hollow body 2 of the receiving sleeve 1 in a force-fit manner only at the contact points 15, the major part of the surface of the portion of the tool 14 received in the receiving sleeve 1 is not in contact with the hollow body 2 of the receiving sleeve 1 so that the cleaning fluid can wash around it.

FIG. 3 finally shows a receiving sleeve 1 which is inserted in the intermediate shelf 16 or in the bottom 20 of the tool set 19 according to the invention. The intermediate shelf 16 and/or the bottom 20 consist(s) of the two metal sheets arranged to be parallel to each other, wherein one metal sheet comprises the stamped hole array 17 and the other metal sheet comprises the array 18 of the cornered recesses which are in alignment with the round holes of the array 17. The surface area of the cornered recess of the array 18 is smaller than the surface area of the round hole of the array 17.

FIG. 3 clearly shows how the positioning studs 8 of the receiving sleeve 1 engage in a respective corner of a cornered recess of the array 18 in a form-fit manner and in this way prevent any rotation of the inserted receiving sleeve 1. In addition, the latching arm 9 engages in a further corner of the cornered recess of the array 18 in a form-fit manner, wherein the hook-shaped protrusion of the latching arm 9 moving under the metal sheet of the array 18 and thus anchoring the receiving sleeve 1 in the intermediate shelf 16 or in the bottom part 20. The radial protrusion of the retaining arm 6 moves under the metal sheet of the array 17 and additionally serves for anchoring the receiving sleeve 1 in the intermediate shelf 16 or bottom part 20.

As already indicated, the distance between the two arrays 17 and 18 is defined by the distance of the protrusions of the latching arm 9 and of the retaining arm 6 upon which the arrays 17 and 18 come to lie, respectively. Here, the array 17 is held in position between the surrounding protrusion/collar 10 and the protrusion of the retaining arm 6, whereas the array 18 is fixed between the hook-shaped protrusion of the latching arm 9 and the circumference of the hollow cylinder 2.

The invention claimed is:

1. A receiving sleeve of a tool set for a supporting mount of surgical tools, the receiving sleeve comprising a cylindrical hollow body having an end face provided with an insertion opening for inserting a tool to be inserted,
the hollow body defining a longitudinal axis and comprising a plurality of circumferentially spaced inner clamping elements which have punctiform or linear engagement sections which are provided at their free ends and adapted for making a force-fit and/or form-fit contact with the tool to be inserted for holding the tool to be inserted within the receiving sleeve at a radial distance from the cylindrical hollow body,
the inner side of the hollow body provided with a plurality of circumferentially spaced rigid protrusions for centering the tool to be inserted in the receiving sleeve, the rigid protrusions extending axially in rib-like fashion and are chamfered like a funnel in the area of the insertion opening, producing an insertion aid for the tool to be inserted,
wherein the inner clamping elements and the rigid protrusions are provided at the inner side of the hollow body and alternate in a circumferential direction of the hollow body so that each inner clamping element is arranged between two rigid protrusions, and each rigid protrusion is arranged between two inner clamping elements.

2. The receiving sleeve according to claim 1, wherein the inner clamping elements are flexible and elastic clamping arms which extend in an axial direction and are formed on the hollow body as a hinge.

3. The receiving sleeve according to claim 1, wherein the receiving sleeve is formed in one piece.

4. The receiving sleeve according to claim 2, wherein the flexible and elastic clamping arms situated on the inner side of the hollow body are made of metal and embedded or inserted in the hollow body of the receiving sleeve.

5. The receiving sleeve according to claim 1, wherein a plurality of circumferentially spaced, rigid positioning studs are formed on the hollow body which extend axially beyond the end face of the receiving sleeve on an end portion of the hollow body opposite the insertion opening.

6. The receiving sleeve according to claim 1, wherein an end portion of the hollow body opposite the insertion opening is provided with at least one further flexible and elastic latching protrusion or latching arm which extends axially beyond the end face of the receiving sleeve.

7. The receiving sleeve according to claim 1, wherein the hollow body is provided in the axial area of the insertion opening with an annular protrusion or collar serving as an axial stop for the receiving sleeve.

8. The receiving sleeve according to claim 7, wherein the annular protrusion or collar comprises axially extending protrusions on a side of the annular protrusion or collar facing axially away from the insertion opening, which serve as punctiform or linear axial supports or spacers.

9. The receiving sleeve according to claim 1, wherein the plurality of rigid protrusions form a catching bottom or stop on an end portion of the receiving sleeve opposite the insertion opening, said catching bottom or stop preventing the tool to be inserted from being inserted too deeply into the receiving sleeve.

10. The receiving sleeve according to claim 1, wherein the inner clamping elements are located closer to the longitudinal axis of the hollow body than the rigid protrusions and the rigid protrusions define a maximum shaft diameter that can be inserted into the receiving sleeve.

11. A surgical tool set for storing and cleaning surgical tools, the surgical tool set comprising:
a reception box comprising a side frame, a bottom part and an intermediate shelf which can be placed in the reception box, the bottom part and/or the intermediate shelf formed as two parallel and spaced, interconnected perforated plates, each of the perforated plates forming an axially aligned hole array;
a cover for closing the reception box; and
a plurality of receiving sleeves inserted in the hole arrays, each receiving sleeve comprising a cylindrical hollow body having an end face provided with an insertion opening for inserting a tool to be inserted, the cylindrical hollow body comprising a plurality of circumferentially spaced inner clamping elements which have punctiform or linear engagement sections which are provided at their free ends and adapted for making a force-fit and/or form-fit contact with the tool to be inserted for holding the tool to be inserted within the receiving sleeve at a radial distance to the cylindrical hollow body, the inner side of the hollow body provided with a plurality of rigid protrusions for centering a surgical instrument in the receiving sleeve, the rigid protrusions extending axially in rib-like fashion and are chamfered like a funnel in the area of the insertion opening, producing an insertion aid for the tool to be inserted.

12. The surgical tool set according to claim 11, wherein at least the box is formed from a perforated material.

13. The surgical tool set according to claim 11, wherein one of the perforated plates has round holes and the other of the perforated plates has cornered holes, such that the receiving sleeves can be inserted or are inserted with their cylindrical hollow bodies into the round holes as a maximum up to the surrounding protrusion or collar, whereas the rigid positioning studs engage the corners of the cornered holes for positioning the receiving sleeves.

14. The surgical tool set according to claim 13, wherein at least one latching arm engages behind said other of the perforated plates when the receiving sleeve is axially inserted to the full extent, wherein the receiving sleeve is axially fixed in the intermediate shelf by the cooperation between the collar and the latching arm.

15. A surgical tool set for storing and cleaning surgical tools, the surgical tool set comprising:
a reception box comprising a side frame, a bottom part and an intermediate shelf which can be placed in the reception box, the bottom part and/or the intermediate shelf formed as two parallel and spaced, interconnected perforated plates, each of the perforated plates forming an axially aligned hole array;
a cover for closing the reception box; and
a plurality of receiving sleeves inserted in the hole arrays, each receiving sleeve comprising a cylindrical hollow body having an end face provided with an insertion opening for inserting a tool to be inserted, the cylindrical hollow body comprising a plurality of circumferentially spaced inner clamping elements which have punctiform or linear engagement sections which are provided at their free ends and adapted for making a force-fit and/or form-fit contact with the tool to be inserted for holding the tool to be inserted within the receiving sleeve at a radial distance to the cylindrical hollow body, the inner side of the hollow body provided with a plurality of rigid protrusions which extend axially in rib-like fashion and are chamfered like a funnel in the area of the insertion opening, producing an insertion aid for the tool to be inserted,
wherein one of the perforated plates has round holes and the other of the perforated plates has cornered holes, such that the receiving sleeves can be inserted or are inserted with their cylindrical hollow bodies into the round holes as a maximum up to the surrounding protrusion or collar, whereas the rigid positioning studs engage the corners of the cornered holes for positioning the receiving sleeves.

16. The surgical tool set according to claim 15, wherein at least one latching arm engages behind said other of the perforated plates when the receiving sleeve is axially inserted to the full extent, wherein the receiving sleeve is axially fixed in the intermediate shelf by the cooperation between the collar and the latching arm.

* * * * *